United States Patent
Scherbring

(10) Patent No.: US 7,628,059 B1
(45) Date of Patent: Dec. 8, 2009

(54) MOBILE TURF INSTRUMENT APPARATUS HAVING DRIVEN, PERIODICALLY INSERTABLE, GROUND PENETRATING PROBE ASSEMBLY

(75) Inventor: David J. Scherbring, Savage, MN (US)

(73) Assignee: The Toro Company, Bloomington, MN (US)

( * ) Notice: Subject to any disclaimer, the term of this patent is extended or adjusted under 35 U.S.C. 154(b) by 0 days.

(21) Appl. No.: 11/986,552

(22) Filed: Nov. 21, 2007

Related U.S. Application Data

(60) Provisional application No. 60/860,583, filed on Nov. 22, 2006.

(51) Int. Cl.
*G01N 3/00* (2006.01)
(52) U.S. Cl. .......................................... 73/84
(58) Field of Classification Search ........................ None
See application file for complete search history.

(56) References Cited

U.S. PATENT DOCUMENTS

| | | | | |
|---|---|---|---|---|
| 3,224,512 A | * | 12/1965 | Alexander | 173/19 |
| 5,591,902 A | * | 1/1997 | Castagner | 73/84 |
| 2003/0083819 A1 | * | 5/2003 | Rooney et al. | 702/5 |
| 2006/0236786 A1 | * | 10/2006 | Burton | 73/863 |

* cited by examiner

*Primary Examiner*—Robert R Raevis
(74) *Attorney, Agent, or Firm*—James W. Miller

(57) ABSTRACT

A mobile turf instrument apparatus has a wheeled frame that may be propelled over the ground by a motive device, such as by a separate vehicle or by its own engine and drive train. A driven arm is carried on the frame and revolves in circles to periodically insert the probe(s) of a probe assembly into the ground during motion of the frame. The drive to the arm is momentarily disengaged when the probe(s) of the probe assembly are inserted into the ground. The probe assembly comprises two parts that rock relative to one another. Two soil measurement devices are connected to the probe assembly. A soil moisture sensor is coupled to the probe assembly for measuring soil moisture when the probe(s) are inserted into the ground. A load cell is responsive to the amount of rocking of the two parts of the probe assembly to measure soil compaction.

15 Claims, 7 Drawing Sheets

MOBILE TURF INSTRUMENT APPARATUS HAVING DRIVEN, PERIODICALLY INSERTABLE, GROUND PENETRATING PROBE ASSEMBLY

CROSS REFERENCE TO RELATED APPLICATIONS

This application claims the benefit of one or more previously filed copending provisional applications identified as follows: Application Ser. No. 60/860,583 filed Nov. 22, 2006.

TECHNICAL FIELD

This invention relates generally to the field of turf maintenance equipment. More particularly, this invention relates to equipment carrying instruments for measuring various parameters related to the health of the turf, such as soil moisture, soil compaction, etc.

BACKGROUND OF THE INVENTION

The turf maintenance field involves a wide range of equipment used to promote turf growth and to thereafter maintain the grass surface forming the upper portion of the turf. For example, aerators are used to punch holes in the ground to relieve soil compaction in and beneath the turf. Mowers are used to cut the grass surface of the turf to a desired height. Fertilizers apply nutrients and pesticides to the turf to encourage grass growth and to prevent or limit damage to the grass by insects.

In order to intelligently diagnose the health of the turf, various measuring instruments are used to measure various parameters related to the health of the turf. For example, many known soil moisture sensors determine the moisture content of the soil using Timed Domain Reflectometry (TDR). A TDR sensor involves sticking a probe assembly comprising various probes into the ground. When the probes are pulsed with electrical energy while they are inserted into the ground, a reading can be taken from which the moisture content of the soil can be derived.

A penetrometer is a type of instrument used to measure soil compaction. Like the TDR sensor described above, a penetrometer has a probe assembly that must be pushed into the ground in order for the penetrometer to take a reading. The penetrometer includes a load cell that measures the resistance the probe assembly encounters when entering the ground. This resistance is a measure of how compacted the soil is at the spot where the probe assembly has been inserted into the ground.

Other turf measurement instruments are known. A spectrometer known as the GreenSeeker® uses light emitting diodes (LED) to generate red and near infrared (NIR) light. The light generated is reflected off of the grass surface of the turf and is measured by a photodiode. Red light is absorbed by plant chlorophyll as an energy source during photosynthesis. Therefore, healthy turf absorbs more red light and reflects larger amounts of NIR than turf that is unhealthy. Thus, the GREENSEEKER® Instrument provides a measurement of the health or vigor of the turf. Other spectrometers besides the GreenSeeker® are also known in the art.

A turf measurement instrument like the GreenSeeker® spectrometer operates without requiring physical penetration of the ground. A spectrometer works simply by shining light at the turf and measuring the reflected light from the grass. Thus, in the past a spectrometer type instrument has simply been mounted on a mobile frame and driven over an area of turf whose health is to be measured.

However, for a TDR soil moisture sensor, the probe assembly must be inserted into the ground in order for the device to operate. Thus, in the past, such an instrument has traditionally been hand held with the probe assembly being manually inserted or pushed into the soil at various desired spots. This is done by a walking operator who holds the instrument in his or her hands and who manually pushes the probe assembly into the soil to undertake a soil moisture measurement and then manually pulls the probe assembly out of the soil at the conclusion of the measurement. This is a difficult and tiring task. Moreover, when measuring the soil moisture content over a large area of turf, such as a golf course, it is extremely time consuming and laborious.

Penetrometers used to measure soil compaction have in the past been mounted on vehicles rather than being hand-held. However, like a TDR soil moisture sensor, the probe assembly of the penetrometer must be inserted into the ground in order to take a reading. Thus, with a vehicle mounted penetrometer, the vehicle must be stopped at each location where a reading is desired, the penetrometer must then be inserted into the ground, the reading is then taken, and then the penetrometer must be pulled out of the ground, all with the vehicle remaining stopped. Then, and only then, can the vehicle be driven to the next spot where a reading is to be taken. While the operator need not walk the entire area to be measured, the need to stop the vehicle at each spot where the penetrometer is to be inserted into the ground still makes the act of measuring a large area of turf a time consuming one.

SUMMARY OF THE INVENTION

One aspect of this invention relates to a mobile turf measurement apparatus. The apparatus comprises a frame propelled over the ground by a motive device other than a walking operator. A probe assembly is movably carried on the frame such that the probe assembly has repeating cycles of motion relative to the frame as the frame is propelled over the ground with the probe assembly being lowered on the frame and approaching towards the ground and being raised on the frame and moving away from the ground during each cycle of motion. The probe assembly has at least one probe that is inserted into the ground as the probe assembly moves towards the ground and that is extracted from the ground as the probe assembly moves away from the ground such that the probe(s) are inserted into the ground for a time interval lasting over only a portion of each cycle of motion of the probe assembly. A soil measurement device is operatively connected to the probe(s) of the probe assembly for measuring a parameter of the soil during the time interval when the probe(s) have been inserted into the ground.

Another aspect of this invention relates to a mobile turf measurement apparatus. The apparatus comprises a frame supported for rolling over the ground by at least one rotatable ground engaging member. A revolving arm is carried on the frame for rotation about a substantially horizontal axis of rotation. A first drive rotates the arm in complete 360° revolutions about the axis of rotation as the frame is moved over the ground. A probe assembly is carried adjacent one end of the revolving arm. The probe assembly includes at least one elongated probe that is inserted into the ground at some point in each revolution of the arm. A first soil measurement device is operatively connected to the probe(s) of the probe assembly for measuring a parameter of the soil when the probe(s) have been inserted into the ground.

An additional aspect of this invention relates to a mobile turf instrument apparatus. The apparatus comprises a frame that may be propelled over the ground by a motive device. A probe assembly has at least one probe. The probe assembly comprises two parts that rock relative to one another. A soil moisture sensor is carried on the probe assembly for measuring soil moisture when the probe(s) are inserted into the ground. A load cell is carried on the probe assembly and is responsive to the amount of relative rocking of the two parts of the probe assembly when the probe(s) are inserted into the ground to measure soil compaction. A driven arm carries the probe assembly. The driven arm is journalled on the frame for rotating about a substantially horizontal axis to periodically insert the probe(s) of the probe assembly into the ground during motion of the frame over the ground.

Yet another aspect of this invention relates to a probe assembly for use in taking soil measurements. The probe assembly comprises a first part and a second part pivotally secured to the first part to be able to rock towards and away from the first part. At least one elongated probe is mounted on the second part with the probe(s) being inserted into the ground to take soil measurements. A soil moisture sensor is operatively connected to the probe(s) for measuring soil moisture when the probe(s) are inserted into the ground. A load measuring device is provided which device is responsive to the relative degree of rocking of the second part relative to the first part to be progressively more loaded as the second part progressively rocks towards the first part during insertion of the probe(s) into the ground to thereby measure soil compaction.

BRIEF DESCRIPTION OF THE DRAWINGS

This invention will be described hereafter in the Detailed Description, taken in conjunction with the following drawings, in which like reference numerals refer to like elements or parts throughout.

DETAILED DESCRIPTION

Figure 1:
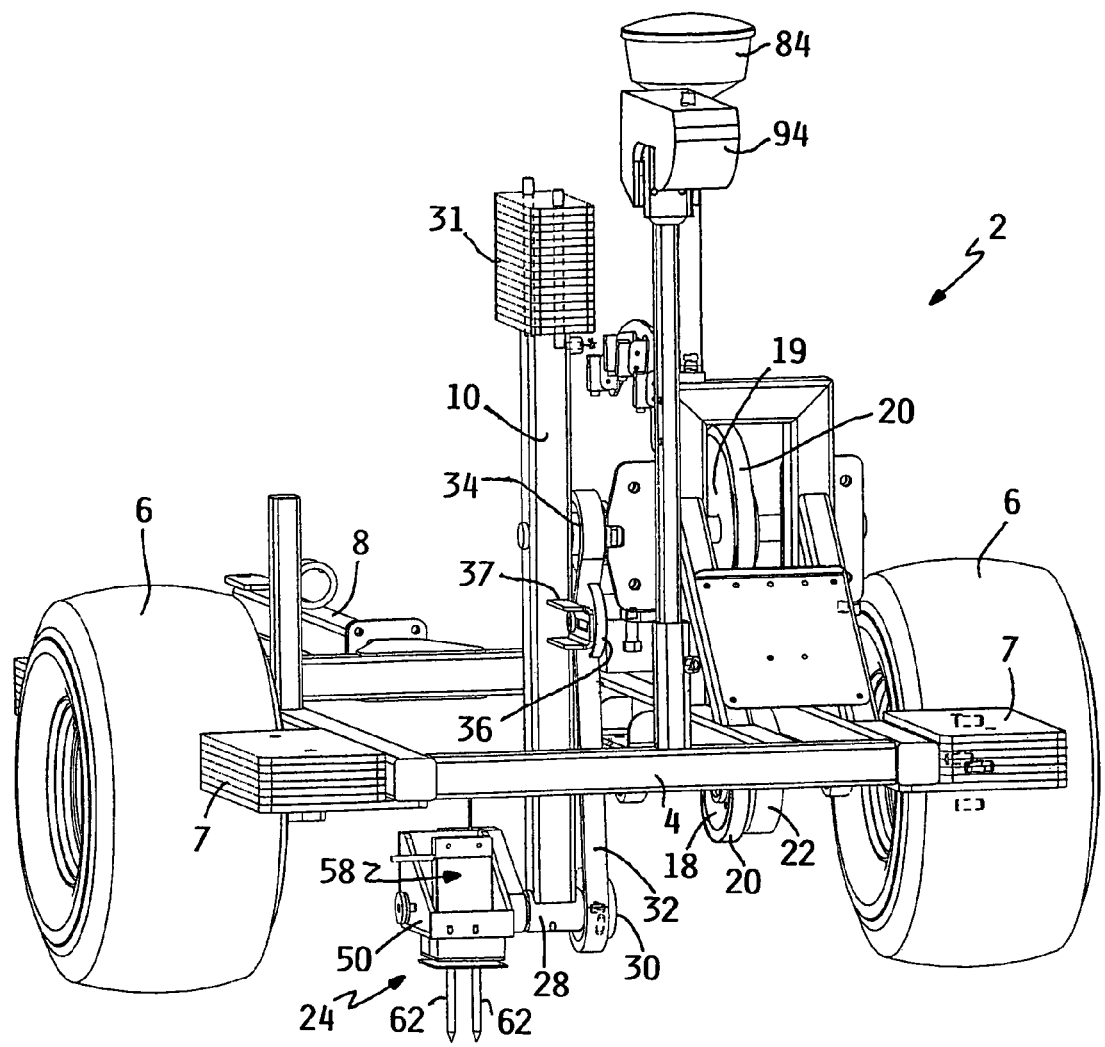
FIG. 1 is a perspective view towards the rear of a mobile turf instrument apparatus according to this invention.
Figure 2:
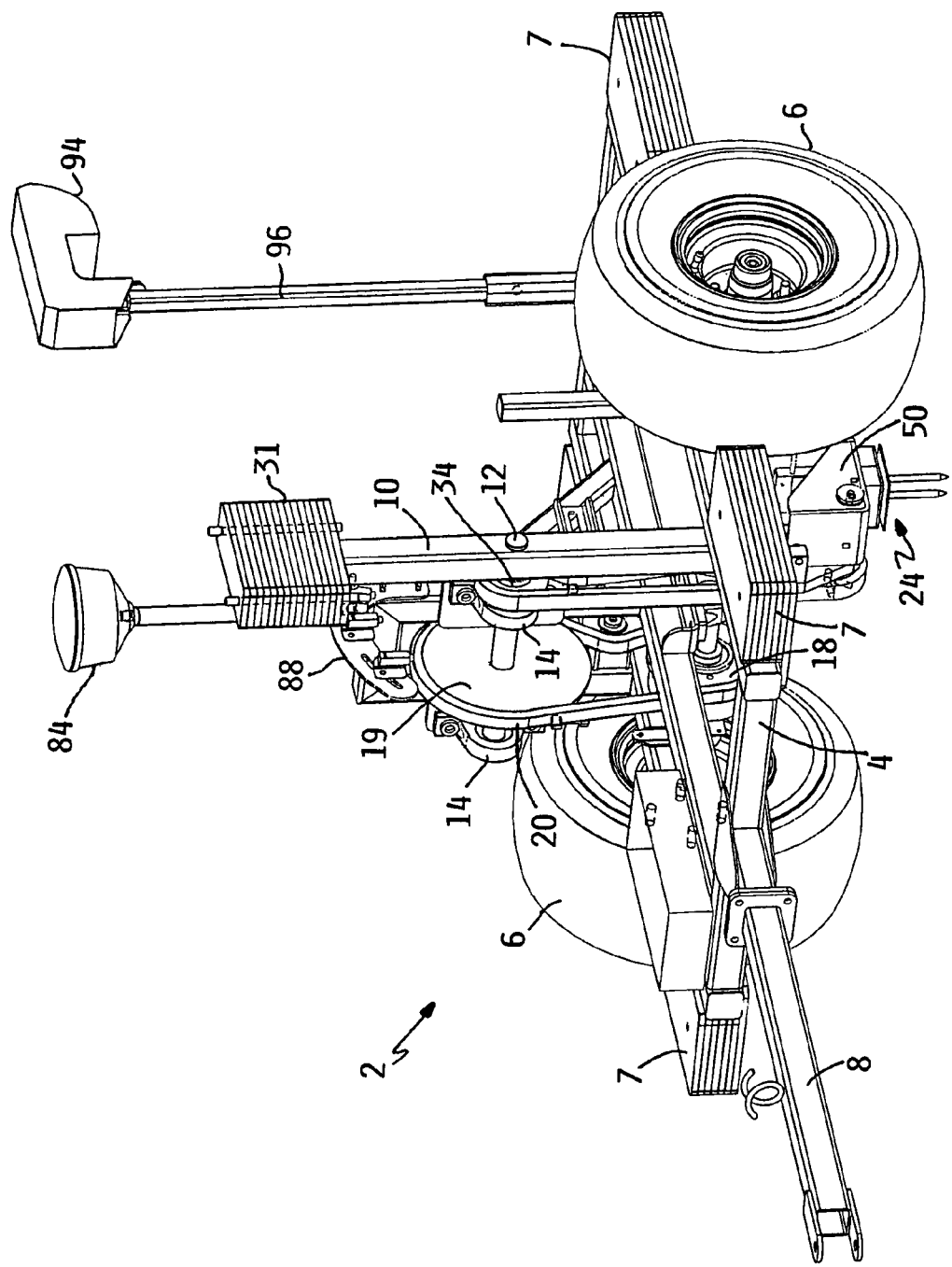
FIG. 2 is a perspective view towards the left front of the mobile turf instrument apparatus of FIG. 1.
Figure 3:
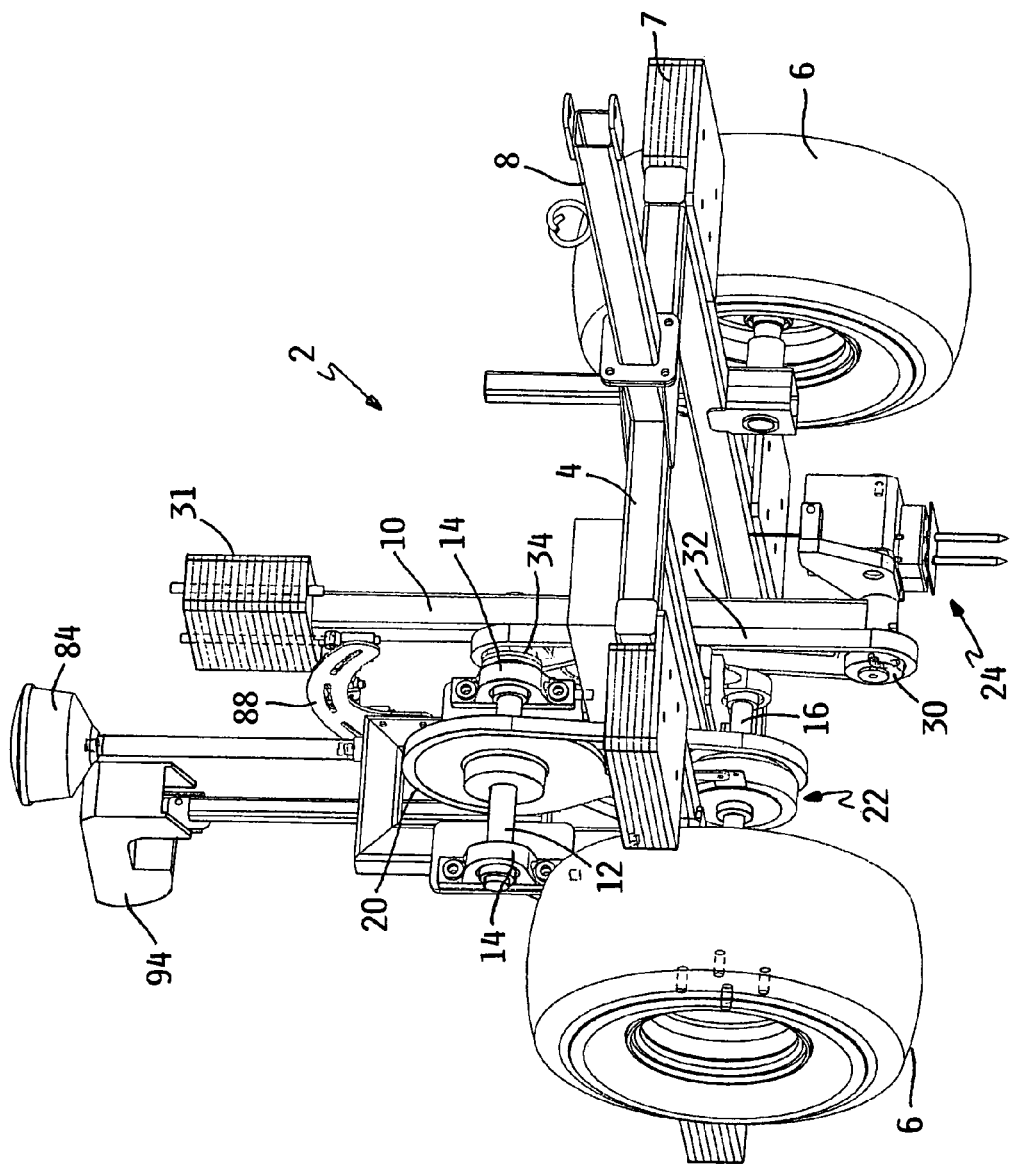
FIG. 3 is a perspective view towards the right front of the mobile turf instrument apparatus of FIG. 1.

FIGS. 1-3 illustrate one embodiment of a mobile turf instrument apparatus 2 according to this invention. Apparatus 2 comprises a mobile platform or frame 4 supported for rolling over the ground by one or more rotatable ground engaging members, such as by a pair of wheels 6. Frame 4 preferably comprises a tow frame having a forwardly extending tongue 8 for allowing frame 4 to be hitched to a motive device in the form of a towing vehicle, such as a mower, utility vehicle, or the like. Alternatively, frame 4 could be pushed by the separate vehicle rather than being towed. Moreover, frame 4 could be self-propelled with the motive device comprising an engine or motor carried on frame 4. Counterweights 7 can be placed on frame 4, preferably at the corners thereof, to add enough weight to frame 4 to prevent frame 4 from bouncing up and down as it is moved over the ground.

Apparatus 2 includes a revolving support in the form of an elongated revolving arm 10. Arm 10 is fixed to an inner end of a substantially horizontal shaft 12 so as to rotate with shaft 12. Shaft 12 extends to one side of frame 4 such that an outer end of shaft 12 is located along one side of frame 4. See FIG. 3. Shaft 12 is rotatably journalled on frame 4 by a pair of spaced bearings 14 carried on frame 4.

Arm 10 is positioned in an open central space in frame 4. In addition, bearings 14 are located high enough on frame 4 such that arm 10 can revolve around the axis of shaft 12 and will clear the ground when doing so. The open central space of frame 4 is also large enough in a fore-and-aft direction to accommodate the revolving motion of arm 10 without arm 10 hitting any part of frame 4.

Arm 10 is revolved by a drive taken from one wheel 6 of frame 4. The stub axle 16 that mounts such wheel 6 is long enough such that the inner end of stub axle 16 is located beneath frame 4 generally parallel to and below shaft 12. See FIG. 3. A first small drive sprocket 18 is carried around stub axle 16 and shaft 12 carries a second larger driven sprocket 19, the two sprockets 18, 19 being connected together by a chain 20. Sprockets 18, 19 are sized to provide a speed reduction between the rotational speed of wheels 6 and that of arm 10.

An electric clutch 22 is also carried on stub axle 16 to selectively drive stub axle sprocket 18. In other words, stub axle sprocket 18 is coupled to stub axle 16 and is rotated by stub axle 16 when clutch 22 is engaged. Conversely, stub axle sprocket 18 is uncoupled from stub axle 16 and is not being rotated by stub axle 16 when clutch 22 is disengaged.

Figure 5:
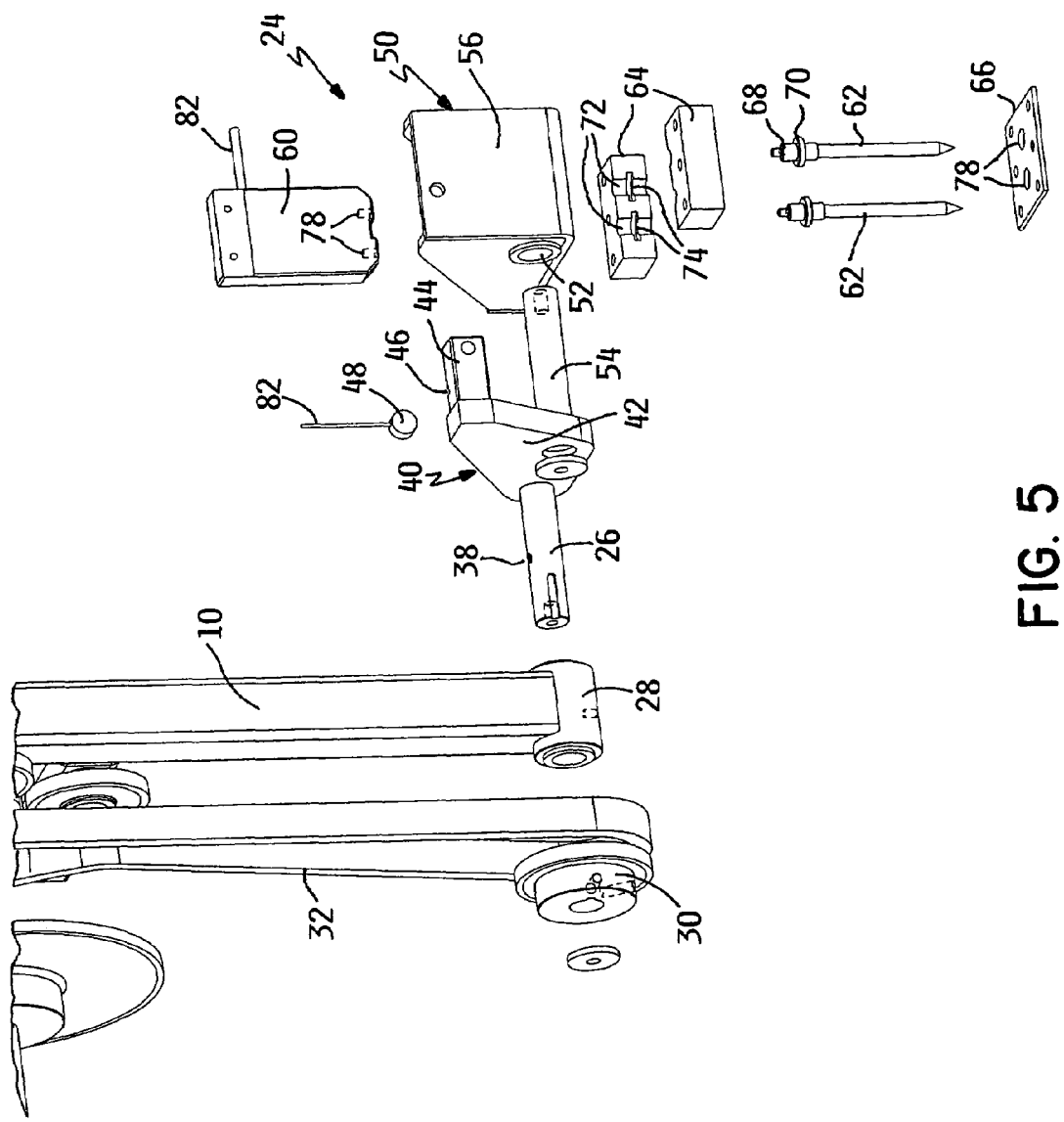
FIG. 5 is an exploded perspective view of the probe assembly of FIG. 4.

Referring now to FIG. 5, a probe assembly indicated generally as 24 is rotatably mounted on one end of arm 10. A pivot shaft 26 on probe assembly 24 extends through a bearing in a hub 28 on the end of arm 10. Pivot shaft 26 is non-rotatably keyed or splined to a small sprocket 30 that is also carried on the end of arm 10. Rotation of probe assembly sprocket 30 relative to the end of arm 10 will also rotate probe assembly 24 relative to the end of arm 10.

The opposite end of arm 10 carries a weight 31. Weight 31 is heavier than the collective weight of probe assembly 24 and sprocket 30 on the other end of arm 10. Thus, when apparatus 2 is stationary and arm 10 is not being revolved by rotation of wheel 6, arm 10 will have a resting position in which weight 31 is lowermost and probe assembly 24 is uppermost, i.e. arm 10 will be vertical and the end of arm 10 carrying weight 31 will be the lower end of arm 10 and the end of arm 10 carrying probe assembly 24 will be the upper end of arm 10. This resting position of arm 10 is not illustrated in the drawings.

Figure 6:
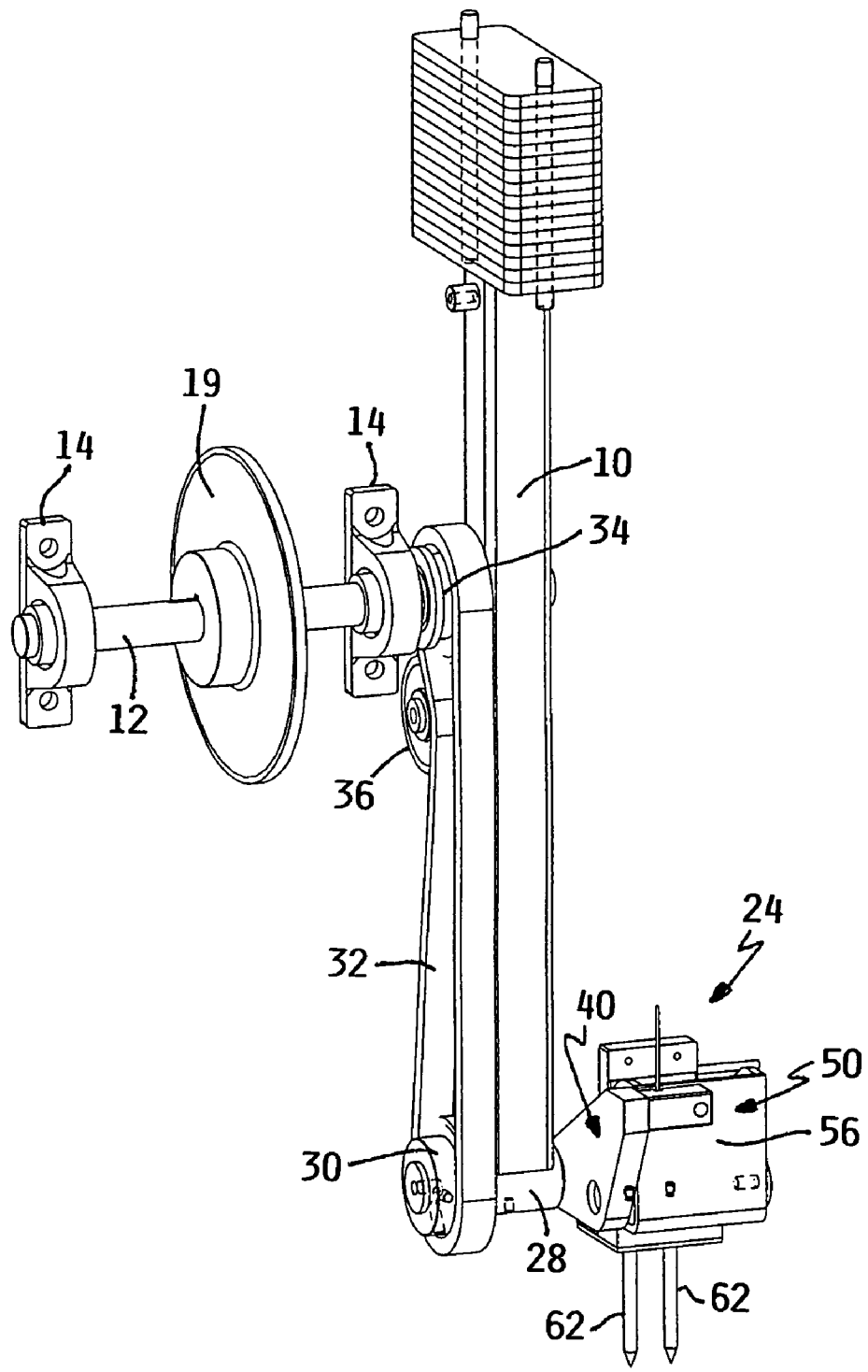
FIG. 6 is a perspective view of the revolving arm that periodically inserts the probe assembly of FIG. 4 into the soil.

Probe assembly sprocket 30 on the end of arm 10 is coupled by a chain 32 to a fixed sprocket 34 that is carried concentrically around horizontal shaft 12 that rotates arm 10. Fixed sprocket 34 is so named because no rotation of sprocket 34 is allowed relative to frame 4. Fixed sprocket 34 is physically clamped or held relative to frame 4 so that it does not rotate. A rotatable idler sprocket 36 is mounted by a bracket 37 on arm 10 substantially immediately beneath fixed sprocket 34. See FIGS. 1 and 6. Idler sprocket 36 helps maintain proper tension on chain 32 during rotation of arm 10.

As arm 10 rotates around horizontal shaft 12 in a given direction, chain 32 produces an equal and opposite counter-rotation of probe assembly sprocket 30 so that probe assembly 24 always remains substantially horizontal relative to frame 4 or to the ground during rotation of arm 10. In other words, a reference mark 38 on the top of probe assembly pivot shaft 26 (shown in FIG. 5) will always remain on the top of shaft 26 whether arm 10 is pointing straight up, straight down, forwards, backwards, or in any direction in between. Thus, probe assembly 24 is self-leveling relative to arm 10 as arm 10 rotates or revolves around the axis of shaft 12.

In a complete revolution of arm 10, chain 32 translates or moves along arm 10 by a distance equal to the number of teeth in fixed sprocket 34 and probe assembly sprocket 30. Fixed sprocket 34 and probe assembly sprocket 30 are identical in size with the same number of teeth. While fixed sprocket 34 does not rotate relative to frame 4 or relative to the ground, fixed sprocket 34 does rotate relative to arm 10 as arm 10 revolves around the axis of shaft 12. One must remember that fixed sprocket 34 is concentrically positioned around shaft 12 to be on the same axis as shaft 12, but fixed sprocket 34 is not rotatably coupled to shaft 12 and is not part of arm 10. Thus, the rotation of arm 10 does produce relative rotation between arm 10 and fixed sprocket 34.

Probe assembly 24 comprises two parts that are further mounted for pivoting relative to one another during operation of probe assembly 24. These two parts comprise an L-shaped bracket 40 having a side wall 42 and a top rail 44 arranged at a perpendicular angle relative to side wall 42. See FIG. 5. Pivot shaft 26 that mounts probe assembly 24 for pivoting on arm 10 is connected to an inner face of side wall 42 of bracket 40. Top rail 44 of bracket 40 includes a recess, slot or cavity 46 for holding a load cell 48, e.g. an Omega Engineering LC302-500 load cell.

The other part of probe assembly 24 comprises a box-shaped housing 50 with an open top. Housing 50 includes a bore 52 for receiving a pivot pin 54 carried on the outer face of side wall 42 of bracket 40, i.e. on the face of side wall 42 that is opposite to the face that carries pivot shaft 26. Pivot pin 54 allows housing 50 to rock back and forth relative to bracket 40.

Figure 4:
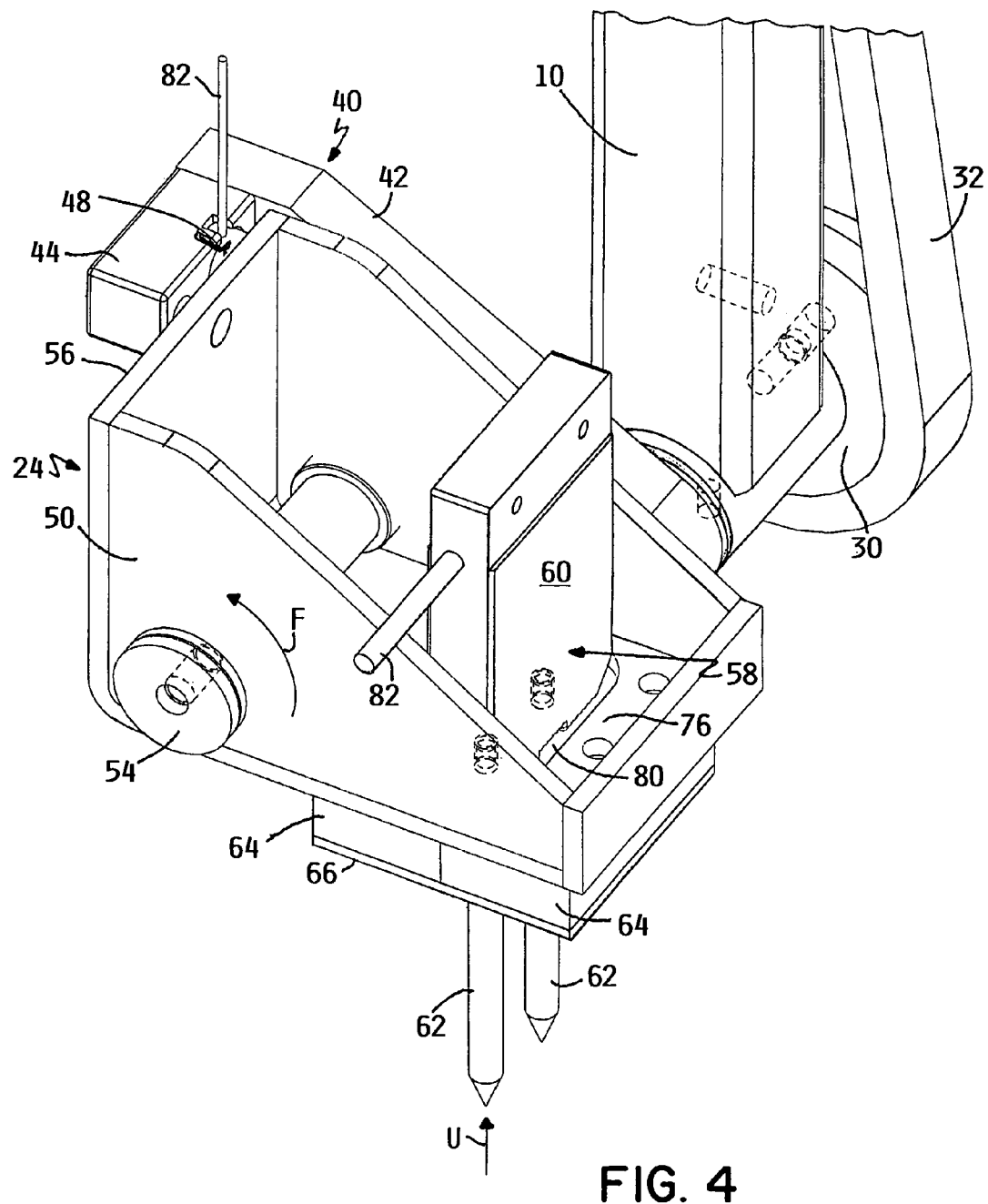
FIG. 4 is a perspective view of the probe assembly of the mobile turf instrument apparatus of FIG. 1.

Referring to FIG. 4, when bracket 40 and housing 50 are assembled together, top rail 44 of bracket 40 is juxtaposed substantially immediately ahead of a front wall 56 of housing 50. Thus, load cell 48 that is held on top rail 44 is positioned to abut with or be closely spaced from front wall 56 of housing 50. As probe assembly 24 is pushed into the ground, rocking of housing 50 about pivot pin 54, depicted by the arrow F in FIG. 4, will vary the force exerted on load cell 48 by housing 50.

A Timed Domain Reflectometer (TDR) soil moisture sensor package 58, e.g. a Campbell Scientific CS620, is carried by housing 50 of probe assembly 24. Sensor package 58 includes a sensor body 60, a pair of ground penetrating probes 62, a pair of probe mounting blocks 64, and a clamping plate 66. Each probe 62 includes a mounting collar 68 around the upper end of probe 62 with the upper end of probe 62 sticking upwardly out of mounting collar 68. Each mounting collar 68 includes an annular, radially extending mounting flange 70. Probes 62 are metallic and mounting collars 68 may be made from any suitably strong and durable material, such as a composite material.

Mounting blocks 64 are provided as a separate pair of blocks 64 to allow blocks 64 to be separated for installation of probes 62. Each mounting block 64 includes a pair of semi-circular grooves 72 with a horizontal channel 74. Each groove 72 is sized to conform to the outer diameter of mounting collar 68 on the upper end of probe 62. Each channel 74 is sized to receive a mounting flange 70 on collar 68. Each mounting block 64 is made of an electrically non-conductive material, such as ABS plastic.

Mounting collars 68 of probes 62 are placed into grooves 72 and channels 74 of one mounting block 64. Then, the other mounting block 64 is superimposed over probes 62 and abutted with the first mounting block 64 to clamp probes 62 between the two mounting blocks 64. Clamping plate 66 is then bolted or screwed to housing 50 to clamp both mounting blocks 64 to the underside of the floor 76 of housing 50. When so mounted, probes 62 will extend downwardly away from housing 50 through openings 78 in clamping plate 66 that are large enough to receive probes 62.

The upper ends of probes 62 project upwardly far enough to reach sensor body 60. Sensor body 60 is positioned or held within housing 50 of probe assembly 24. Sensor body 60 is provided with a pair of threaded probe connections 78 on the bottom of sensor body 60 for receiving the upper threaded ends of probes 62 to establish both a mechanical and electrical connection to probes 62. See FIG. 5. Sensor body 60 can reach the upper ends of probes 62 through a slot 80 provided in floor 76 of housing 50. Thus, effectively sensor body 60 is carried on the upper ends of probes 62 with the upper ends of probes 62 sticking up into probe connections 78 on sensor body 60. Probes 62 are preferably first inserted through slot 80 and screwed into sensor body 60 while sensor body 60 sits in housing 50 and then mounting blocks 64 are abutted around probes 62 beneath housing 50 with clamping plate 66 finally being bolted to housing 50 to hold everything in place.

The upward force exerted on probes 62 as they are inserted into the ground, represented by the arrow U in FIG. 4, is transmitted through mounting collars 68 and mounting blocks 64 to the underside of housing 50. Thus, damage to sensor body 60 from the force U generated during probe insertion is either eliminated or greatly reduced. Mounting collars 68, mounting blocks 64, and how mounting blocks 64 are abutted and bolted to housing 50 are a simple and durable mounting system for probes 62 and sensor body 60.

It should be clear that both load cell 48 and sensor body 60 are electrically connected to various control and measurement electronics located elsewhere. These electrical connections are diagrammatically illustrated by electrical wires 82. Thus, the readings that are derived from load cell 48 and sensor package 58 can be logged or recorded in any appropriate device, such as a data logger or computer (not shown). The computer may be carried on frame 4 itself, or on the vehicle used to tow the frame 4, and may be hardwired to load cell 48 and sensor body 60 as suggested by wires 82. Alternatively, wireless communication could be established between load cell 48 and sensor body 60 to allow the readings to be wirelessly communicated to the computer.

As frame 4 moves across the turf, and when clutch 22 is engaged, arm 10 will rotate or revolve from the drive taken from wheel 6. As arm 10 revolves, probe assembly 24 rotates correspondingly in a way that maintains probe assembly 24 in a horizontal position with probes 62 facing the ground. At some point, arm 10 will approach the ground and probes 62 will be pushed into the ground.

Clutch 22 can be disengaged to uncouple arm 10 from the drive from wheel 6 from some time shortly before probes 62 have entered the ground (assuming arm 10 has sufficient momentum) to some time shortly after probes 62 have entered the ground. If clutch 22 is disengaged shortly before probes 62 have entered the ground and the speed of the arm is high enough, then the momentum of arm 10 will be sufficient to cause arm 10 to continue to rotate and to insert probes 62 in the ground. Once probes 62 are inserted into the ground, then arm 10 will still continue to rotate since probes 62 are now stuck in the ground but frame 4 is continuing its forward motion. Thus, when the drive is actually disconnected from arm 10 from a moment just prior to or just after probe insertion and/or during the entire time probes 62 are in the ground, arm 10 will to the naked eye look like it is revolving as before.

There are two reasons for disconnecting the drive to arm 10 while probes 62 are inserted into the ground. One is to avoid having probes 62 make elongated holes or slots in the ground. The other is to avoid putting too much torque or stress on probes 62 or on the other components of sensor package 58 while probes 62 are in the ground. This will further help avoid damaging probes 62 or the other components of sensor package 58.

In any event, the drive disconnection to arm 10 lasts only so long as probes 62 are in the ground. When arm 10 swings around past bottom dead center and probe assembly 24 is about to begin to lift probes 62 out of the ground, clutch 22 is reengaged. This couples arm 10 to the drive from wheel 6 to continue the rotation of arm 10 again.

When probes 62 of probe assembly 24 are in the ground, electrical energy can be supplied to probes 62 from the control electronics to initiate a soil moisture measurement. This measurement will then be reported back to the computer as described above and will be recorded. A GPS device 84 or other global locating device can be carried on frame 4. Thus, the reported soil moisture reading can be correlated to the location where the reading was taken.

This is also true of the readings of any other turf parameters that will be taken and recorded. Such readings will similarly be correlated to the GPS location of frame 4 at the time they are taken. Thus, an accurate map can be made of the turf area over which frame 4 is moved which map will display the various readings of the measured turf parameters and where such readings occurred.

Load cell 48 positioned between housing 50 and bracket 40 of probe assembly 24 is used to measure soil compaction when probes 62 are being inserted in the ground. This is so because the force exerted on load cell 48 by housing 50 will vary depending upon the hardness of the ground. The rocking action of housing 50 determines the force on load cell 48 and the rocking action varies depending upon the hardness of the ground. Housing 50 will rock more during probe insertion when the ground is hard as opposed to when the ground is soft. Thus, a measurement of soil compaction can be taken and recorded along with the soil moisture reading. Thus, the same probe assembly 24 does double duty since it functions both as part of a penetrometer used to measure soil compaction as well as part of a soil moisture sensor.

Figure 7:
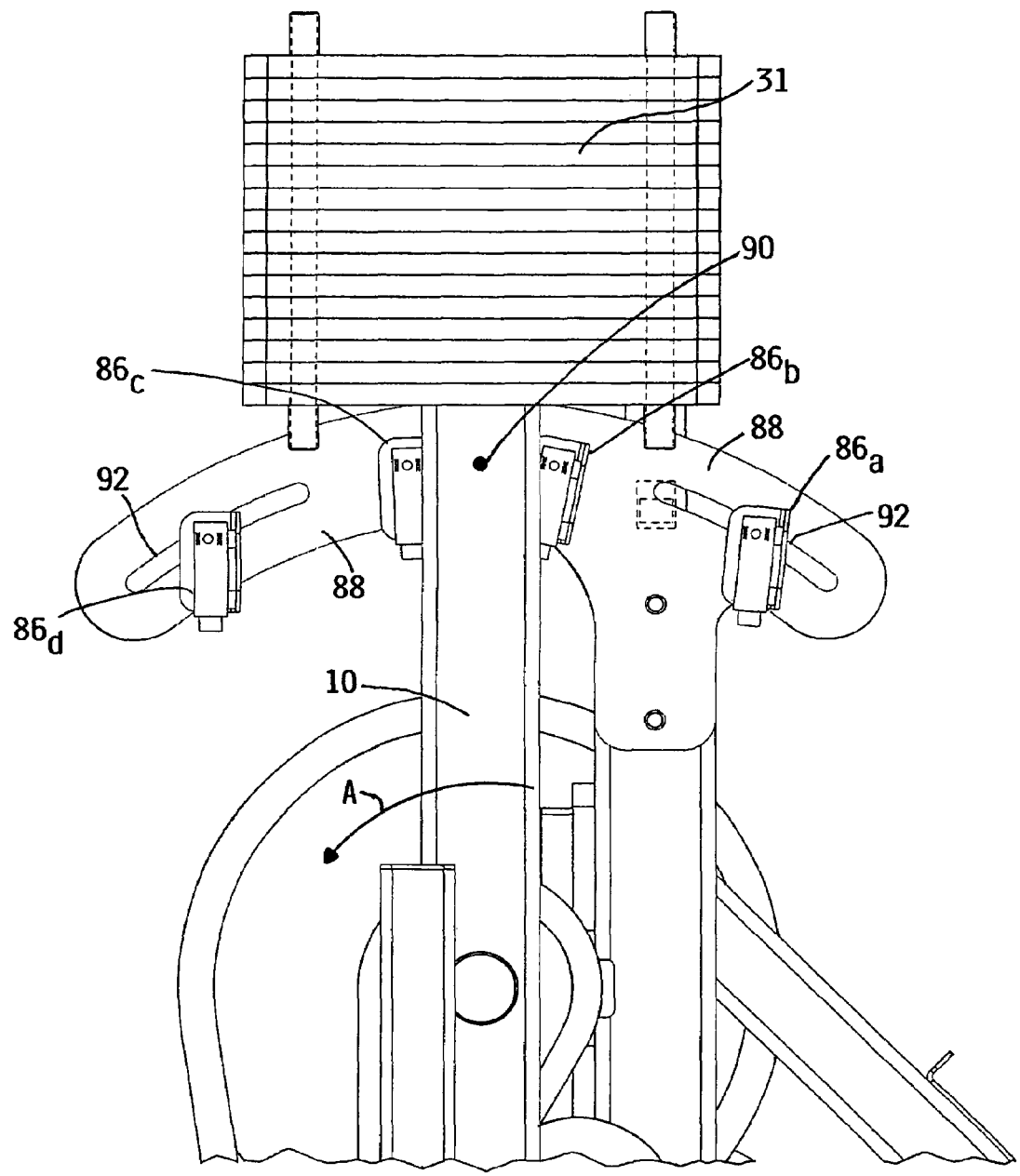
FIG. 7 is a side elevational view of the controls that engage and disengage the drive to the revolving arm of FIG. 6 and that start and stop the taking of readings from various turf measurement instruments carried on the arm.

Referring now to FIG. 7, a plurality of limit switch controls 86 are mounted in a fixed position on frame 4 along an arcuate flange 88. Flange 88 is positioned symmetrically relative to the top dead center position of arm 10 as shown in FIG. 7. Each limit switch 86 senses or is triggered by a magnetic or other trigger 90 carried on arm 10. Thus, as arm 10 revolves in the direction of rotation indicated by the arrow A in FIG. 7, limit switches 86 will be selectively closed in sequence beginning with the first limit switch $86_a$ and ending with the fourth limit switch $86_d$.

The first and fourth limit switches $86_a$ and $86_d$ control the engagement and disengagement of clutch 22 respectively. In other words, when the first limit switch $86_a$ is tripped shortly after probe assembly 24 enters the ground, clutch 22 will be disengaged. As the fourth limit switch $86_d$ is tripped as probe assembly 24 just begins to lift out of the ground, clutch 22 will be engaged. The precise positioning of the first and fourth limit switches $86_a$ and $86_d$ can be adjusted by sliding them back and forth in arcuate slots 92 carried on flange 88. This allows the user to adjust the disengagement of clutch 22 to correspond to when probes 62 have just been inserted into the ground and to adjust the engagement of clutch 22 to when probes 62 are just about to lift out of the ground.

The second and third limit switches $86_b$ and $86_c$ signal to the control electronics when to start and stop the soil moisture and soil compaction sensing. Sensing starts when second limit switch $86_b$ is tripped. Sensing stops when third limit switch $86_c$ is tripped. The second and third limit switches $86_b$ and $86_c$ could be replaced, however, with a time delay following tripping of first limit switch $86_a$. In other words, sensing could start and stop during a predetermined time interval that begins after a predetermined time delay following the tripping of first limit switch $86_a$.

In addition to measuring and recording parameters that are derived from the insertion of probe assembly 24 into the ground, frame 4 could carry other turf instruments that do not depend upon such an insertion. For example, a spectrometer 94 for measuring the health of the grass could be mounted on frame 4 at any suitable location, such as on a post 96 on the rear of frame 4. As frame 4 moves over the ground, spectrometer 94 measures the vigor or health of the turf using light reflectance as described in the Background of the Invention section of this application. Such a turf health measurement reading would then be correlated to the GPS location of frame 4 and stored with the soil moisture and soil compaction readings in the overall map of the turf area being surveyed. These turf health measurement readings could be taken at the same time as the soil moisture or compaction readings or at different times.

Apparatus 2 of this invention provides for measuring various parameters of the turf using a probe assembly 24 that is periodically inserted into and removed from the ground. It does so, however, by mounting such a probe assembly on a mobile frame to allow the readings derived from probe assembly 24 to be accomplished automatically and without effort by the operator as frame 4 is driven or otherwise moved over the turf area to be surveyed and measured. This greatly enhances the productivity of the operator. The operator need not walk the turf area by foot and stick a hand held soil moisture sensor into the ground. The vehicle need not be stopped to allow the probe assembly to be inserted into the ground.

In addition, frame 4 can be used to carry other turf measurement instruments, such as spectrometer 94, that measure other turf parameters using methods that do not require physical penetration of the ground or in fact any engagement with the turf or the ground. Thus, apparatus 2 of this invention can provide a whole range of turf parameter measurements and record and map such measurements over the turf area being surveyed. Obviously, sensors other than those described herein for measuring other turf parameters could be added to frame 4 of apparatus 2. For example, instruments for measuring soil salinity or canopy temperature could be added.

Various modifications of this invention will be apparent to those skilled in the art. While a simple mechanical drive from wheel 6 is preferred for rotating arm 10, arm 10 could be driven by a separate hydraulic or electric motor. Soil moisture sensors other than TDR soil moisture sensors could be used. Thus, this invention is not limited to the specific details of the embodiment disclosed herein.

The invention claimed is:
1. A mobile turf measurement apparatus, which comprises:
   (a) a frame propelled over the ground by a motive device other than a walking operator;
   (b) a probe assembly movably carried on the frame such that the probe assembly has repeating cycles of motion relative to the frame as the frame is propelled over the ground, wherein the probe assembly is lowered on the frame and moves towards the ground and is raised on the frame and moves away from the ground during each cycle of motion;

(c) at least one probe carried on the probe assembly with the probe(s) being inserted into the ground as the probe assembly moves towards the ground and being extracted from the ground as the probe assembly moves away from the ground such that the probe(s) are inserted into the ground for a time interval lasting over only a portion of each cycle of motion of the probe assembly; and (d) a soil measurement device operatively connected to the probe(s) of the probe assembly for measuring a parameter of the soil during the time interval when the probe(s) have been inserted into the ground.

2. The apparatus of claim 1, wherein the probe assembly is oriented with the probe(s) substantially continuously facing the ground during the repeating cycles of motion.

3. The apparatus of claim 1, further including a drive for propelling the probe assembly through the repeating cycles of motion, wherein the drive is disengaged for a substantial portion of the time interval.

4. A mobile turf instrument apparatus, which comprises:
   (a) a frame supported for rolling over the ground by at least one rotatable ground engaging member;
   (b) a revolving arm carried on the frame for rotation about a substantially horizontal axis of rotation;
   (c) a first drive to rotate the arm in complete 360° revolutions about the axis of rotation as the frame is moved over the ground;
   (d) a probe assembly carried adjacent one end of the revolving arm, wherein the probe assembly includes at least one elongated probe that is inserted into the ground at some point in each revolution of the arm; and
   (e) a first soil measurement device operatively connected to the probe(s) of the probe assembly for measuring a parameter of the soil when the probe(s) have been inserted into the ground.

5. The apparatus of claim 4, wherein the probe assembly is rotatably carried on the arm, and further including a second drive to rotate the probe assembly in a direction counter to the direction of rotation of the arm as the arm is revolving to thereby keep the probe(s) of the probe assembly substantially facing the ground.

6. The apparatus of claim 5, wherein the second drive comprises an endless member entrained around a portion of the frame and a portion of the probe assembly for producing the counter rotation of the probe assembly from the revolving motion of the arm as the first drive rotates the arm.

7. The apparatus of claim 6, wherein the second drive comprises:

(a) a first toothed sprocket non-rotatably coupled to the probe assembly such that rotation of the first toothed sprocket rotates the probe assembly on the arm;
(b) a second toothed sprocket fixed to the frame, wherein the first and second sprockets have the same number of teeth; and
(c) wherein the endless member is a chain entrained around the first and second toothed sprockets.

8. The apparatus of claim 7, wherein the second toothed sprocket is fixed to the frame and lies along the axis of rotation of the arm.

9. The apparatus of claim 4, further including a clutch for disengaging the first drive at least during a substantial portion of a time interval defined between a first moment in time when the probe(s) are inserted into the ground and a second moment in time when the probe(s) are extracted from the ground during each revolution of the arm.

10. The apparatus of claim 9, further including a pair of first and second circumferentially spaced limit switches carried on the frame adjacent an orbital path of the arm as the arm revolves on the frame, wherein the first and second limit switches are tripped by the arm as the arm revolves to control the clutch to thereby sequentially disengage and reengage the first drive.

11. The apparatus of claim 4, wherein the first drive is powered from at least one of the ground engaging member(s) of the frame.

12. The apparatus of claim 11, wherein the first drive includes a speed reduction such that the arm revolves more slowly than the speed of rotation of the ground engaging member(s) from which the first drive is powered.

13. The apparatus of claim 4, further including a weight carried adjacent an end of the arm opposite to the end of the arm carrying the probe assembly, wherein the weight has a mass sufficiently high such that the end of the arm carrying the probe assembly will be elevated to a raised, substantially vertically upright position when the arm is at rest and the first drive for revolving the arm is not operating.

14. The apparatus of claim 4, wherein the first soil measurement device is selected from a group of devices comprising a soil moisture sensor and a soil compaction measurement device.

15. The apparatus of claim 14, further including a second soil measurement device operatively connected to the probe(s) of the probe assembly for measuring a parameter of the soil when the probe(s) have been inserted into the ground, wherein the first soil measurement device comprises the soil moisture sensor and the second soil measurement device comprises the soil compaction measurement device.

* * * * *